(12) United States Patent
Albert et al.

(10) Patent No.: US 6,183,721 B1
(45) Date of Patent: Feb. 6, 2001

(54) CHELATED PEPTIDES, COMPLEXES THEREOF, PHARMACEUTICAL COMPOSITIONS CONTAINING THEM AND THEIR USE AS RADIOPHARMACEUTICALS

(75) Inventors: Rainer Albert, Basel (CH); Christian Bruns, Freiburg (DE); Peter Smith-Jones, Basel (CH); Barbara Stolz, Freiburg (DE); Gisbert Weckbecker, Biel-Benken (CH)

(73) Assignee: Novartis AG, Basel (CH)

( * ) Notice: Under 35 U.S.C. 154(b), the term of this patent shall be extended for 0 days.

(21) Appl. No.: 08/842,125

(22) Filed: Apr. 23, 1997

Related U.S. Application Data

(63) Continuation of application No. 08/522,875, filed on Sep. 1, 1995, now abandoned.

(51) Int. Cl.[7] .................... A61K 51/00; A61M 36/14

(52) U.S. Cl. ............... 424/1.69; 424/1.65; 530/328; 530/311; 534/15

(58) Field of Search .................... 242/1.11, 1.65, 242/1.69, 9.1; 530/328–330, 300–327, 311, 317; 534/7, 10–16; 540/450; 562/1; 514/9, 1

(56) References Cited

U.S. PATENT DOCUMENTS

| 5,006,643 | 4/1991 | Fazio et al. . | |
|---|---|---|---|
| 5,219,555 | 6/1993 | Bremer et al. . | |
| 5,428,154 | * 6/1995 | Gansow et al. | 540/465 |
| 5,650,134 | * 7/1997 | Albert et al. | 424/1.69 |
| 5,705,143 | * 1/1998 | Bower et al. | 424/1.69 |

FOREIGN PATENT DOCUMENTS

| 0515313 | 11/1992 | (EP) . |
| 0607103 | 7/1994 | (EP) . |
| 2225579 | 6/1990 | (GB) . |

OTHER PUBLICATIONS

Mather et al (1992), Cell Biophysics, vol. 21, pp. 93–107, "Radiolabeled Octreotide".*

Lewis et al (1994), Bioconjugate Chem., vol. 5, No. 6, pp. 565–576, "A Facile, Water Soluble Method for Modification of Proteins with DOTA. Use of Elevated Temperature and Optimized pH to Achieve High Specific Activity and High Chelate Stability in Radiolabeled Immunoconjugates."*

Kline, et al., Bioconjugate Chemistry, vol. 2, pp. 26–31 (1991).

Lewis, et al., Bioconjugate Chemistry, vol. 5, No. 6, pp. 565–576 (1994).

Li, et al., Bioconjugate Chemistry, vol. 4, pp. 275–283 (1993).

Li, et al., Bioconjugate Chemistry, vol. 5, No. 2, pp. 101–104 (1994).

Sherry, et al., Inorganic Chemistry, vol. 28, No. 3, pp. 620–622 (1989).

Meares, et al., Br. J. Cancer, vol. 62, Suppl. X, pp. 21–26 (1990).

* cited by examiner

Primary Examiner—Dameron Jones
(74) Attorney, Agent, or Firm—Joseph J. Borovian

(57) ABSTRACT

Compounds of formula I

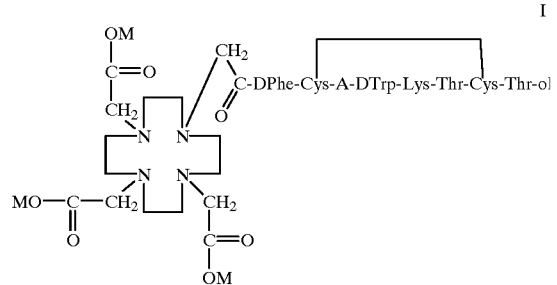

wherein

M is a cation equivalent and A is Phe or Tyr, in free form or in salt form are useful as radiopharmaceuticals when complexed with a radionuclide.

19 Claims, No Drawings

CHELATED PEPTIDES, COMPLEXES THEREOF, PHARMACEUTICAL COMPOSITIONS CONTAINING THEM AND THEIR USE AS RADIOPHARMACEUTICALS

This is a continuation of application Ser. No. 08/522,875, filed Sep. 1, 1995 now abandoned.

The present invention relates to somatostatin peptides, a process for their production, pharmaceutical preparations containing them and their use as a radiopharmaceutical, e.g. for radiotherapy of somatostatin receptor positive tumors.

Radiotherapy of tumors with radioactive compounds has the advantages of selectively targeting tumors and their metastases, thus limiting the radiation dose to normal tissue. A radiotherapeutic agent should have a fast accumulation and high retention at the target organs, e.g. tumor, and a fast clearance from the circulation to limit the whole body radiation dose. A radiotherapeutic agent based on a chelated radiometal should also be thermodynamically and/or kinetically stable against loss of the radiometal. A radiotherapeutic agent being administered repeatedly should not be immunogenic.

GB-A-2,225,579 discloses somatostatin peptides bearing at least one chelating group which can be radiolabelled for in vivo diagnostic and therapeutic applications. These compounds are capable of binding to somatostatin receptors, e.g. expressed or overexpressed by tumors or metastases. EP-A2-607,103 describes somatostatin peptides comprising a bifunctional polyaminopoly-carboxylic acid chelating group attached to their terminal amino group by means of a spacer group. However, even though the presence of a bifunctional chelating group (octadentate) and of a spacer group lead to the improvement of certain properties of the resulting conjugate, there is still a compelling need for a radiopharmaceutical with further improved properties, particularly a high target/kidney ratio to minimize the radiation dose in the kidneys.

It has now been found that somatostatin peptides as disclosed hereinafter comprising a monofunctional DOTA (1,4,7,10-tetra-azacyclododecane-1,4,7,10-tetraacetic acid) conjugated directly, i.e. in the absence of a spacer group, to the terminal amino group of the somatostatin peptides have improved properties. Particularly they have an improved tumor/kidney ratio hence a lower radiation dose delivered to the kidneys.

According to the invention there is provided a compound of formula I

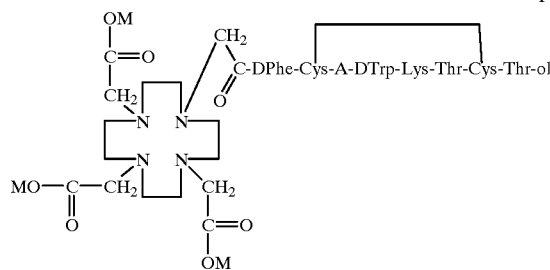

wherein
M is H$^+$ or a cation and
A is Phe or Tyr,
in free form, salt form or complexed with a radionuclide.

As it will be appreciated, each bond

connecting 2 nitrogen atoms in the DOTA formula above represents ethylene.

When A is Phe, the peptide moiety of the compound of formula I corresponds to octreotide. When A is Tyr, the peptide moiety corresponds to [Tyr$^3$]-octreotide.

A is preferably Tyr. M may be H$^+$ or any salt forming cation for a carboxy group, e.g. a monovalent or one equivalent of a polyvalent cation, for example an alkali metal ion such as sodium, potassium, or a substituted or unsubstituted ammonium ion.

Compounds of formula I may also exist e.g. in the form of an internal salt when M is H$^+$ or in the form of acid addition salts. Acid addition salts include e.g. salts obtained by addition of an organic, polymeric or inorganic acid, for example chlorhydrate, acetate, trifluoroacetate or lactate.

By radionuclide is meant an α- or β-emitting nuclide or a nuclide with Auger-e$^-$-cascades. Suitable nuclides include e.g. $^{64}$Cu, $^{67}$Cu or a radiolanthanide, particularly $^{90}$Y, $^{140}$La, $^{161}$Tb, $^{169}$Er, $^{153}$Sm, $^{177}$Lu, $^{166}$Dy, $^{166}$Ho or $^{175}$Yb, more preferably $^{161}$Tb and $^{90}$Y, most preferably $^{90}$Y.

The present invention also includes a process for the production of the compounds of formula I. They may be produced by analogy to known methods. The compounds of formula I may be produced for example as follows:

a) removing at least one protecting group which is present in a compound of formula I in protected form, or b) linking together by an amide bond two peptide units, one of them containing at least one amino alcohol in protected or unprotected form and the other of them containing the DOTA group, wherein the amide bond is in such a way that the desired amino acid sequence of formula I is obtained, and stage a) of the process is then optionally effected, or c) linking together DOTA and the desired somatostatin peptide in protected or unprotected form in such a way that the group derived from DOTA is fixed on the terminal amino group of the peptide, and stage a) is then optionally effected or, d) oxidizing a DOTA-peptide having the amino acid sequence as stated in formula I wherein the mercapto groups of the Cys radicals exist in free form so as to produce a compound of formula I in which the 2 Cys radicals are joined by an S-S-bridge, and recovering the compounds of formula I thus obtained in free form, in salt form or in complexed form with a radionuclide.

The above reactions may be effected in analogy with known methods, e.g. as described in the following examples. Where desired, in these reactions, protecting groups which are suitable for use in peptides or for the DOTA chelating group may be used for functional groups which do not participate in the reaction. The term protecting group may also include a polymer resin having functional groups. DOTA may be used in process step (c) in the free acid form, as an anhydride or as an activated ester, e.g. with N-hydroxysuccinimide.

The complexation with the radionuclide may be performed at room temperature in accordance with methods known in the art, e.g. by reacting an uncomplexed compound of formula I with a salt yielding the desired radionuclide.

Preferably the complexation of the uncompleted compound of formula I with the radionuclide-yielding salt is effected at a temperature of from 60° to 120° C., more preferably from 80 to 100° C. When the complexation is performed at a temperature $\geq 100°$ C., it may be effected in an autoclave. The complexation under heating may conveniently be carried out for a short time period, e.g. from 10 to 20 minutes. When the radionuclide is $^{90}$Y, the preferred $^{90}$Y-yielding salt is $^{90}$YCl$_3$.

The above mentioned reactions may conveniently be effected under conditions avoiding trace metal contamination. Preferably distilled de-ionized water, ultrapure reagents, no carrier-added radioactivity etc. are used to reduce the effects of trace metal.

The compounds of formula I, when complexed with a radionuclide, exhibit pharmaceutical activity and are therefore useful as a radiopharmaceutical for the in vivo treatment of somatostatin receptor positive tumors and metastases as indicated by standard tests.

In particular, the compounds of formula I possess affinity for somatostatin receptors which can be assessed in vitro in binding assays performed as disclosed by J. C. Reubi, Life Sc. 36, 1829 (1985) and by C. Bruns et al. in Biochem. J., 265, 39 (1990).

It is observed that the compounds of formula I, e.g. a compound of formula I complexed with $^{90}$Y or $^{161}$Tb, bind with a good affinity and specificity to somatostatin receptors with $pK_D$ values of from about 8.0 to 10.0.

Compound of Example 1 binds with high affinity to somatostatin receptors expressed in rat cortex or AR42J pancreatic tumor cells: it has a pKi of $8.9 \pm 0.1$ using [$^{125}$I][Tyr$^3$]-octreotide as specific ligand. Compound of Example 2 is a somatostatin receptor specific ligand that can be displaced from the somatostatin receptors by octreotide: $pIC_{50} = 9.0 \pm 0.3$.

The affinity of the complexed compounds of formula I for somatostatin receptors can also be shown by in vivo testing, according to standard test methods, e.g. as disclosed in GB-A-2, 225,579. For example, in one trial, the compound of Example 2 gives a significant tumor accumulation 2 hours following i.p. injection at a dose of 5 $\mu$Ci into mice bearing an exocrine pancreatic tumor: $9.05 \pm 0.61$% ID/g present in the somatostatin receptor positive tumor whereas significantly less radioactivity is accumulated in somatostatin receptor positive normal tissues, e.g. in the pancreas it amounts $1.52 \pm 0.08$% ID/g. By % ID/g is meant the percentage of the injected radioactivity dose per g tissue. Not only does Compound of Example 2 provide 24 hours after injection a high tumor/kidney ratio but also a high tumor/liver and tumor/femur ratio. Bone marrow being regarded as the most radiosensitive organ, the low radioactivity accumulated in bones is particularly surprising.

The compounds of formula I complexed with a radionuclide have an antiproliferative effect on tumor cells bearing somatostatin receptors, e.g. as indicated in nude mice tests.

AR42J rat pancreatic tumor cells are trypsinized and $1 \times 10^7$ tumor cells (in 0.2 ml) are injected subcutaneously into both flanks of nude mice. When tumors have reached a significant volume of 0.1 to 2 ml, animals are randomized into control and treatment groups. Control animals, receive either an uncomplexed compound of formula I or the corresponding cold complexed compound of formula I by i.p. injections at doses corresponding to the highest dose of the treatment groups. Doses from 0.8 mCi up to 40 mCi/kg/100 $\mu$l are given per mouse. The size of the tumors is determined with a caliper. To calculate the tumor volume in ml the equation "volume (ellipsoid)=length×depth×height× 0.52" is used. For statistical calculations Student's t-test is applied. In this test, transient tumor shrinkage up to 70% is observed after one week and tumor growth is delayed for two weeks upon a single application of the compound of Example 2. In contrast, the control groups showed continuous tumor growth with a volume doubling time about seven days. The survival rate of the treated groups is significantly increased.

Similar results are obtained when treating mice or rats bearing other tumor types, e.g. mammary carcinomas or small cell lung cancer, with Compound of Example 2.

Accordingly, in a series of specific or alternative embodiments, the present invention also provides:

1. Use of a compound of formula I complexed with a radionuclide or a pharmaceutically acceptable salt thereof, as a radiopharmaceutical for in vivo treatment of somatostatin receptor positive tumors and metastases.
2. A method for in vivo treatment of somatostatin positive tumors and metastases, e.g. for treating invasiveness of such tumors or symptoms associated with such tumor growth, in a subject in need of such treatment which comprises administering to said subject a therapeutically effective amount of a compound of formula I complexed with a radionuclide or a pharmaceutically acceptable salt thereof.
3. Use of a compound of formula I or a pharmaceutically acceptable salt form in the manufacture of a radiopharmaceutical composition.

Dosages employed in practicing the radiotherapeutic use of the present invention will of course vary depending e.g. on the particular condition to be treated, for example the known radiosensitivity of the tumor type, the volume of the tumor and the therapy desired. In general, the dose is calculated on the basis of radioactivity distribution to each organ and on observed target uptake. A $\beta$-emitting complex of formula I may be administered at several time points e.g. over a period of 1 to 3 weeks or longer.

In animals, an indicated dosage range may be of from 0.1 to 1 $\mu$g/kg compound of formula I complexed e.g. with 0.1 to 2 mCi $^{90}$Y or $^{161}$Tb. In larger mammals, for example humans, an indicated dosage range is of from 5 to 100 $\mu$g compound of formula I complexed with e.g. 10 to 100 mCi $^{90}$Y or $^{161}$Tb, the higher radioactivity range being preferred for $^{161}$Tb.

The compounds of formula I complexed with a radionuclide may be administered by any conventional route, in particular intravenously, e.g. in the form of injectable solutions or suspensions. They may also be administered advantageously by infusion, e.g. an infusion of 30 to 60 min. Depending on the site of the tumor, they may be administered as close as possible to the tumor site, e.g. by means of a catheter. They may also be administered repeatedly in divided doses.

Tumors which may be treated with compounds of formula I complexed with a radionuclide are e.g. pituitary, gastro-enteropancreatic, carcinoids, central nervous system, breast, prostatic, ovarian or colonic tumors, small cell lung cancer, paragangliomas, kidney cancer, skin cancer, neuroblastomas, pheochromocytomas, medullary thyroid carcinomas, myelomas, lymphomas, Hodgkins and non-Hodgkins disease, bone tumors and metastases thereof.

Excretion of the radioactive compounds essentially takes place through the kidneys. Further protection of the kidneys from radioactivity accumulation may be achieved by administration of lysine or arginine or an amino acid solution having a high content of lysine and/or arginine, e.g. a commercially available amino acid solution such as Vamina® 18EF or Synthamin®-14 or -10, prior to the injection of or together with the complexed compound of formula I.

Compounds of formula I complexed with a radionuclide may exist in free acid form or as pharmaceutically acceptable salts which exhibit the same order of activity as the complexes in free acid form.

Compound of Example 1 complexed with $^{90}$Y is preferred.

According to a further aspect of the invention, there is provided a pharmaceutical composition comprising a compound of formula I or a compound of formula I complexed with a radionuclide, or a pharmaceutically acceptable salt thereof together with one or more pharmaceutically acceptable carriers or diluents therefor. Such compositions may be manufactured in conventional manner.

According to a preferred embodiment of the invention, the pharmaceutical compositions based on a compound of formula I complexed with a radionuclide further comprise a stabilizer, e.g. a free radical scavenger, which inhibits autoradiolysis of the peptide moiety. Suitable stabilizers include e.g. serum albumine, ascorbic acid, retinol, gentisic acid or a derivative thereof, or an amino acid infusion solution, e.g. as used for parenteral protein feeding, preferably free from electrolyte and glucose, for example a commercially available amino acid infusion such as Proteinsteril® KE Nephro. Ascorbic acid is preferred. The stabilizer may conveniently be used in a weight ratio of 1,000–10,000:1, preferably 4000–7000:1 to the uncomplexed compound of formula I. The pharmaceutical compositions may comprise further additives, e.g. an agent to adjust the pH between 7.2 and 7.4, e.g. Na or ammonium acetate or $Na_2HPO_4$. Preferably the stabilizer is added to the uncomplexed compound of formula I and the complexation with the radionuclide is performed in the presence of the stabilizer, either at room temperature or, preferably, at a temperature of from 60 to 120° C. The complexation may conveniently be performed under air free conditions, e.g. under $N_2$ or Ar. Further stabilizer may be added to the composition after complexation.

Compounds of formula I complexed with a radionuclide may also be used in the treatment of autoimmune or inflammatory disorders exhibiting somatostatin receptors, e.g. rheumatoid arthritis.

According to a further embodiment of the invention, the compounds of formula I complexed with a radionuclide may be employed as adjunct or adjuvant to cytostatic therapy, e.g. in combination with a cytostatic agent, preferably a cytostatic agent which enhances the radiotherapy effects by acting as a radiosensitizer. Examples of suitable cytostatic or radiosensitizing agents include e.g. cisplatin, 5-fluorouracil, cyclophosphamide and doxorubicin.

In accordance with the foregoing, the present invention provides in a yet further aspect:

4. A method for treating somatostatin receptor positive tumor invasiveness or symptoms associated with such tumor growth, in a subject in need of such treatment which method comprises administering to said subject an effective amount of a) a compound of formula I complexed with a radionuclide or a pharmaceutically acceptable thereof and b) a second drug substance, said second drug substance being a cytostatic agent.

5. A therapeutic combination, e.g. a kit, for use in treating tumor invasiveness or symptoms associated with tumor growth, said combination including a pharmaceutical composition comprising a compound of formula I complexed with a radionuclide or a pharmaceutically acceptable salt thereof and further including at least one pharmaceutical composition comprising a cytostatic agent.

The cytostatic agent may be used in any amount known to be an effective cytostatic or radiosensitizing amount. The cytostatic agent may be added concomitantly or at a sequenced regimen with the radiopharmaceutical of formula I.

Furthermore, the uncomplexed compounds of formula I show GH-release inhibiting activity as indicated by the inhibition of GH release in vitro from cultured pituitary cells. Anterior pituitary glands from adult male rats are cut into small pieces and dispersed using 0.1% trypsin in 20 mM HEPES buffer. The dispersed cells are cultured for four days in MEM (Gibco) supplemented with 5% fetal calf serum, 5% horse serum, 1 mM $NaHCO_3$, 2.5 nM dexamethasone, 2.5 mg/ml insulin and 20 U/ml Pen/Strep. On the day of the experiment, the attached cells are washed two times with Krebs-Ringer medium buffered with 20 mM HEPES and supplemented with 5 mM glucose and 0.2% BSA. Subsequently the cells are incubated for two to four hours with the test compound in the presence of $3\times10^{-10}$M growth hormone releasing factor. The amount of growth hormone released into the medium is measured by RIA. Uncomplexed compounds of formula I inhibit the release of GH concentration-dependent from $10^{-10}$ to $10^{-6}$ M. Compound of Example 1 has an $IC_{50}$ of 1.6±0.9 nM.

Uncomplexed compounds of formula I are accordingly indicated for use in the treatment of disorders with an aetiology comprising or associated with excess GH-secretion, e.g. in the treatment of acromegaly as well as in the treatment of diabetes mellitus.

For the above uses, satisfactory results in animals are in general obtained at a daily dosage from about 0.03 to 300 μg/kg animal body weight. In larger mammals, for example in humans, an indicated daily dosage is in the range from about 2 μg to about 20 mg, preferably about 0.01 to about 20 mg, e.g. about 10 to about 5000 μg s.c. of the compound conveniently administered in divided doses up to 4 times a day in unit dosage form containing for example from about 0.5 μg to about 10 mg, e.g. from about 2 μg to 10 mg, of the compound or in sustained release form. The uncomplexed compounds of formula I may be administered by any conventional route, for example parenterally e.g. in form of injectable solutions or suspensions, or in a nasal or a suppository form.

The following examples are illustrative of the invention. All temperatures are in ° C. Following abbreviations are employed:

Fmoc=9-fluorenylmethoxycarbonyl

Boc=tert-butoxycarbonyl

DOTA=1,4,7,10-tetra-azacyclododecane-1,4,7,10-tetraacetic acid

DMF=dimethylformamide

Octreotide = H-DPhe-Cys-Phe-DTrp-Lys-Thr-Cys-Thr-ol

EXAMPLE 1

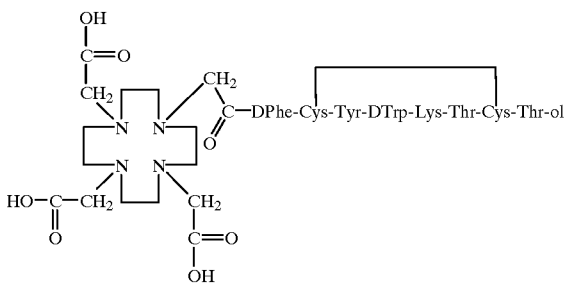

6 g of DOTAx2H$_2$O (free acid) is dissolved in 50 ml of water (pH~3.7). After diluting with 60 ml of DMF, 1 g of N-hydroxy-succinimide, 2.7 g of N,N-dicyclohexylcarbodiimide (DCCI) and 3 g of [Tyr$^3$, ε-Boc-Lys$^5$]-octreotide is added immediately. The reaction is kept at room temperature for 72 hours under continuous stirring. The ε-Lys$^5$ protected compound is isolated by purification on a silica gel 60 column using methylene chloride/methanol/acetic acid 50% (9/1/0.125) as mobile phase.

Subsequent cleavage of the Lys$^5$ protecting group with trifluoroacetic acid (TFA, 100%) over a period of 10 minutes at room temperature and purification on a silica gel 60 column (mobile phase: methylene chloride/methanol/acetic acid 50% (7/3/1 to 7/5/2)) and on a RP18-HPLC column, using water/acetonitrile/acetic acid 1% as buffer system, results in a pure and homogeneous title compound in its acetate salt form. FAB-MH$^+$: 1421 $[\alpha]^D_{22}$=−14.75° (95% AcOH; c=0.52)

EXAMPLE 2

$^{90}$Y Labelled Compound of Example 1

The $^{90}$Y labelled CHELATE is prepared by adding 20 μl of $^{90}$Y (1.2 mCi, 0.04 M HCl) to 20 μL of 50 μM compound of Example 1 (0.15 M NH$_4$OAc, 0.3% BSA, pH 4.5). This solution is incubated at 100° for 15 minutes. An aliquot is removed and diluted with 4 mM DTPA (pH 4.5) before being analyzed by C18 reverse phase HPLC to ascertain the amount of free unchelated $^{90}$Y in the reaction mixture (as indicated by the presence of [$^{90}$YDTPA]$^{2-}$). The radiochemical purity is typically >99.5% and the produced chelate is kinetically stable in 4 mM DTPA (4 nM compound of Example 1, pH 4.5) over a seven day period.

EXAMPLE 3

$^{90}$Y-labelled Compound of Example 1

120 μl of 0.23 M ascorbic acid, 0.15 M ammonium acetate (pH 4.8), 6 μl of 1 mM compound of Example 1 and 120 μl of $^{90}$Y (85 mCi/ml, 0.04 M HCl) are heated in a vial for 15 minutes in a boiling water bath. The resulting solution is diluted to 1 ml with either 0.23 M ascorbic acid and 0.15 M NH$_4$OAc or Proteinsteril® KE Nephro amino acid infusion solution and stored at ambient temperature for long term.

The Proteinsteril® KE Nephro amino acid solution comprises: 11.4 g/l Leu, 9.63 g/l Lys, 9.53 g/l Val, 7.76 g/l Phe, 7.52 g/l Ile, 6.78 g/l Thr, 6.59 g/l Met, 4.9 g/l His and 2.91 g/l Trp.

EXAMPLE 4

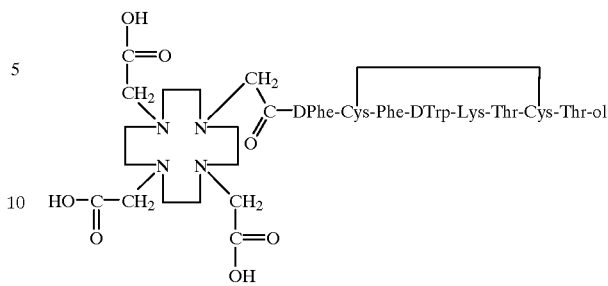

The title compound is obtained by repeating the procedure of Example 1 but using ε-Boc-Lys$^5$-octreotide.
MS (Ion Spray): 1403 (M-H)

EXAMPLE 5

$^{90}$Y Labelled Compound of Example 4

The labelling procedure of example 2 is repeated, thus yielding the $^{90}$Y chelate.

EXAMPLE 6

$^{161}$Tb Labelled Compound of Example 1 or 4

The labelling procedure of example 2 is repeated using a $^{161}$Tb yielding salt instead of the $^{90}$Y yielding salt, thus giving the $^{161}$Tb chelate.

What is claimed is:
1. A compound of formula I

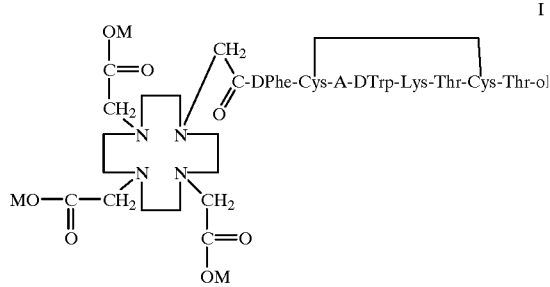

wherein
M is H$^{30}$ or a cation and
A is Tyr, in free form, salt form or complexed with a radionuclide.

2. A compound according to claim 1, which compound is complexed with $^{90}$Y.

3. A compound according to claim 1, which compound is complexed with $^{161}$Tb.

4. A compound according to claim 2 in the acetate salt form.

5. A method for the in vivo treatment of somatostatin positive tumors and metastases in a subject in need of said treatment which comprises administering to said subject a therapeutically effective amount of a compound according to claim 1 complexed with a radionuclide.

6. A method according to claim 5 wherein the compound administered is complexed with $^{90}$Y.

7. A method according to claim 5 wherein the compound administered is complexed with $^{161}$Tb.

8. A method according to claim 5 in which a cytostatic agent is administered with the compound of formula I.

9. A pharmaceutical composition comprising a compound according to claim 1 or a pharmaceutical acceptable salt thereof and a pharmaceutically acceptable carrier therefor.

10. A pharmaceutical composition comprising a compound according to claim 1 complexed with a radionuclide, a stabilizer, and a pharmaceutically acceptable carrier therefor.

11. A composition according to claim 9 wherein the compound is complexed with $^{90}$Y.

12. A composition according to claim 9 wherein the compound is complexed with $^{161}$Tb.

13. A composition according to claim 10, wherein the stabilizer is selected from the group consisting of serum albumin, ascorbic acid, retinol, gentisic acid, and an amino acid solution.

14. A composition according to claim 10, wherein the stabilizer is present in a weight ratio of 1000–10,000:1 to the uncomplexed compound of formula I.

15. A process for complexing a compound according to claim 1 with $^{90}$Y or $^{161}$Tb, which process comprises reacting the compound of formula I with an $^{90}$Y- or $^{161}$Tb-yielding compound at a temperature from 60 to 120° C. in the presence of a stabilizer.

16. A compound according to claim 1 wherein M is H$^+$.

17. A compound according to claim 1 wherein M is sodium, potassium or a substituted or unsubstituted ammonium ion.

18. A compound according to claim 1 in pharmaceutically acceptable salt form.

19. A compound according to claim 1 which is complexed with a radionuclide.

* * * * *

UNITED STATES PATENT AND TRADEMARK OFFICE
CERTIFICATE OF CORRECTION

PATENT NO.    : 6,183,721 B1  
DATED         : February 6, 2001  
INVENTOR(S)   : Albert et al.

Page 1 of 1

It is certified that error appears in the above-identified patent and that said Letters Patent is hereby corrected as shown below:

<u>Title page,</u>
There should be listed as follows:

-- [30] Foreign Application Priority Data
    Sept. 6, 1994  [GB]    United Kingdom...................... 9417873.8 --

<u>Column 8,</u>
Line 48, should read -- M is $H^+$ or a cation and --

Signed and Sealed this

Second Day of April, 2002

*Attest:*

JAMES E. ROGAN
*Attesting Officer*   *Director of the United States Patent and Trademark Office*